(12) United States Patent
Kottenmeier et al.

(10) Patent No.: US 11,596,415 B1
(45) Date of Patent: Mar. 7, 2023

(54) SYSTEMS AND METHODS FOR EMBOLIZATION PROCEDURES FOR TREATMENT OF DEFECTS IN THE VASCULATURE

(71) Applicant: DePuy Synthes Products, Inc., Raynham, MA (US)

(72) Inventors: Emilie Kottenmeier, Laguna Beach, CA (US); Shelly Ikeme, West Chester, PA (US); Rahul Khanna, Naperville, IL (US); Xiaozhou Fan, Orange, CT (US); Sudhakar Satti, Philadelphia, PA (US)

(73) Assignee: DEPUY SYNTHES PRODUCTS, INC., Raynham, MI (US)

( * ) Notice: Subject to any disclaimer, the term of this patent is extended or adjusted under 35 U.S.C. 154(b) by 0 days.

(21) Appl. No.: 17/471,834

(22) Filed: Sep. 10, 2021

(51) Int. Cl.
*G16H 10/60* (2018.01)
*G16H 40/20* (2018.01)
*A61B 17/12* (2006.01)
*A61M 25/10* (2013.01)
*G16H 50/70* (2018.01)

(52) U.S. Cl.
CPC ....... *A61B 17/12186* (2013.01); *A61M 25/10* (2013.01); *A61M 2025/105* (2013.01); *G16H 10/60* (2018.01); *G16H 40/20* (2018.01); *G16H 50/70* (2018.01)

(58) Field of Classification Search
CPC ............ A61B 17/12186; A61M 25/10; A61M 2025/105; G16H 40/20; G16H 10/60; G16H 50/70
See application file for complete search history.

(56) References Cited

U.S. PATENT DOCUMENTS

2021/0038231 A1   2/2021   Walsman

FOREIGN PATENT DOCUMENTS

WO   2020/160469 A1   8/2020

OTHER PUBLICATIONS

Kominami S, Watanabe A, Suzuki M, Mizunari T, Kobayashi S, Teramoto A. Preoperative Embolization of Meningiomas with N-Butyl Cyanoacrylate. Interventional Neuroradiology. 2012;18(2):133-139. doi:10.1177/159101991201800202 (Year: 2018).*

Salaskar, A.L., Razjouyan, F., Cho, A.L. et al. Single institutional experience of peripheral applications of a liquid embolic agent: Ethylene Vinyl Alcohol Copolymer. CVIR Endovasc 3, 38 (2020). https://doi.org/10.1186/s42155-020-00117-2 (Year: 2020).*

(Continued)

*Primary Examiner* — Michael Tomaszewski
*Assistant Examiner* — Mohmad Muqueeth
(74) *Attorney, Agent, or Firm* — Troutman Pepper Hamilton Sanders LLP

(57) ABSTRACT

Methods and systems including an N-butyl cyanoacrylate ("n-BCA") liquid embolic agent and achieving, by the n-BCA liquid embolization agent, a reduction in total cost of preoperative embolization procedures for a plurality of patients versus an ethylene vinyl alcohol copolymer ("EVOH") liquid embolic agent. Methods and systems for reducing supply costs of preoperative embolization by at least approximately 18% are described.

24 Claims, 17 Drawing Sheets

(56) References Cited

OTHER PUBLICATIONS

Loh, Y., & Duckwiler, G. R. (2010). A prospective, multicenter, randomized trial of the Onyx liquid embolic system and N-butyl cyanoacrylate embolization of cerebral arteriovenous malformations, Journal of Neurosurgery JNS, 113(4), 733-741. (Year: 2010).*
Beheshti, MV et al. "Calculation of operating expenses for conventional transarterial chemoembolization in an academic medical center: a step toward defining value of TACE" JBIR Abstract 118, S58-S59 (2014).
Dalyai, R., et al. "Smoking is a negative predictor of arteriovenous malformation posttreatment obliteration: analysis of vascular risk factors in 774 patients" Neurosurgical Focus 37(3): E3, 6 pages, (2014).
Jagadeesan, B. D., et al. "Safety and Feasibility of Balloon-Assisted Embolization with Onyx of Brain Arteriovenous Malformations Revisited: Personal Experience with the Scepter XC Balloon Microcatheter" Interventional Neurology 7:439-444 (2018).
Kim, S. T., et al. "Onyx Embolization of Dural Arteriovenous Fistula, using Scepter C Balloon Catheter: a Case Report" Neurointervention 8:110-114 (2013).
Loh, Y., et al. "A prospective, multicenter, randomized trial of the Onyx liquid embolic system and N-butyl cyanoacrylate embolization of cerebral arteriovenous malformations" J Neurosurg 113:733-741 (2010).
Lv, X., et al. "Complication risk of endovascular embolization for cerebral arteriovenous malformation" European Journal of Radiology 80:776-779 (2011).
Lv, X., et al. "Hemorrhage risk after partial endovascular NBCA and ONYX embolization for brain arteriovenous malformation" Neurological Research 34(6):552-556 (2012).
Raymond, J., et al. "Embolization as One Modality in a Combined Strategy for the Management of Cerebral Arteriovenous Malformations" Interventional Neuroradiology 11:57-62 (2005).
Saatci, I., et al. "Endovascular treatment of brain arteriovenous malformations with prolonged intranidal Onyx injection technique: long-term results in 350 consecutive patients with completed endovascular treatment course" J Neurosurg 115: 78-88 (2011).
Siekmann, R. Basics and Principles in the Application of Onyx LD Liquid Embolic System in the Endovascular Treatment of Cerebral Arteriovenous Malformations: Interventional Neuroradiology 11:131-140 (2005).
Velat, G. J., et al. "Comparison of N-Butyl Cyanoacrylate and Onyx for the Embolization of Intracranial Arteriovenous Malformations: Analysis of Fluoroscopy and Procedure Times" Operative Neurosurgery 1 63: ONS73-80 (2008).
Weber, W., et al. "Endovascular Treatment of Intracranial Arteriovenous Malformations with Onyx: Technical Aspects" AJNR Am J Neuroradiol 28: 371-377 (2007).
Miller, T. R., et al. "Onyx embolization with the Apollo detachable tip microcatheter: A single-center experience" Interv Neuroradiol 24(3):339-344 (2018).
Gailloud, P., "Endovascular Treatment of Cerebral Arteriovenous Malformations" Techniques in Vascular and Interventional Radiology 8(3):1 18-128 (2005).
Extended European Search Report issued in European Patent Application No. 22 19 4905 dated Jan. 17, 2023.

* cited by examiner

| Characteristics<br>N (standard deviation) | | Pre-Match | | Post-Match | |
|---|---|---|---|---|---|
| | | Group 1<br>(N=140) | Group 2<br>(N=932) | Group 1<br>(N=130) | Group 2<br>(N=333) |
| Age | | 47.06 (15.72) | 46.80 (16.65) | 47.65 (15.54) | 46.65 (16.25) |
| Gender | Male | 64 (45.7) | 487 (52.3) | 57 (43.8) | 158 (47.4) |
| Race | White | 84 (60.0) | 613 (65.8) | 80 (61.5) | 202 (60.7) |
| | African American | 23 (16.4) | 128 (13.7) | 22 (16.9) | 62 (18.6) |
| | Other | 33 (23.6) | 191 (20.5) | 28 (21.5) | 69 (20.7) |
| Elixhauser score | | 1.39 (1.41) | 1.58 (1.40) | 1.42 (1.43) | 1.39 (1.28) |
| Surgical resection | | 9 (6.4) | 59 (6.3) | 9 (6.9) | 19 (5.7) |
| Diagnosis related groups | 026: Craniotomy and endovascular intracranial procedures with CC | 19 (13.6) | 185 (19.8) | 19 (14.6) | 50 (15.0) |
| | 025: Craniotomy and endovascular intracranial procedures with MCC | 24 (17.1) | 177 (19.0) | 24 (18.5) | 57 (17.1) |
| | 027: Craniotomy and endovascular intracranial procedures without CC/MCC | 91 (65.0) | 546 (58.6) | 83 (63.8) | 222 (66.7) |
| | 003: ECMO or tracheostomy with MV >96 hours or PDX except face, mouth and neck with major O.R. procedure | 3 (2.1) | 16 (1.7) | 3 (2.3) | 2 (0.6) |
| | Other | 3 (2.1) | 8 (0.9) | 1 (0.8) | 2 (0.6) |

Pre-match, a total of 1072 patents met all inclusion and exclusion criteria.
A total of 463 patients were matched for outcome analysis (Group 1, N=130; Group 2, N=333).

Fig. 2

| Characteristics<br>N (standard deviation) | | Pre-Match | | Post-Match | |
|---|---|---|---|---|---|
| | | Group 1<br>(N=140) | Group 2<br>(N=932) | Group 1<br>(N=130) | Group 2<br>(N=333) |
| Payor category | Commercial | 16 (11.4) | 101 (10.8) | 15 (11.5) | 42 (12.6) |
| | Medicare/Medicaid | 109 (77.9) | 754 (80.9) | 103 (79.2) | 255 (76.6) |
| | Self/Other | 15 (10.7) | 77 (8.3) | 12 (9.2) | 36 (10.8) |
| Procedure Type | Non-Elective | 34 (24.3) | 228 (24.5) | 29 (22.3) | 73 (21.9) |
| Hospital Location | Urban | 137 (97.9) | 896 (96.1) | 127 (97.7) | 322 (96.7) |
| Hospital Type | Teaching | 96 (68.6) | 715 (76.7) | 92 (70.8) | 245 (73.6) |
| Hospital Bed Size | 1-299 | 9 (6.4) | 96 (10.3) | 9 (6.9) | 32 (9.6) |
| | 300-499 | 62 (44.3) | 167 (17.9) | 52 (40.0) | 102 (30.6) |
| | 500 | 69 (49.3) | 669 (71.8) | 69 (53.1) | 199 (59.8) |
| Provider Region | Midwest | 11 (7.9) | 103 (11.1) | 11 (8.5) | 35 (10.5) |
| | Northeast | 15 (10.7) | 265 (28.4) | 15 (11.5) | 43 (12.9) |
| | South | 87 (62.1) | 490 (52.6) | 82 (63.1) | 218 (65.5) |
| | West | 27 (19.3) | 74 (7.9) | 22 (16.9) | 37 (11.1) |

Pre-match, a total of 1072 patents met all inclusion and exclusion criteria.
A total of 463 patients were matched for outcome analysis (Group 1, N=130; Group 2, N=333).

Fig. 3

| Characteristic | | Standardized Mean Difference (SMD)* | |
|---|---|---|---|
| | | Pre-matching | Post-matching |
| Age | 46.84 (± 16) | 0.016 | 0.054 |
| Gender | Male | 0.176 | -0.022 |
| Race | White | 0.074 | -0.028 |
| | African American | -0.120 | 0.048 |
| | Other | 0.075 | -0.021 |
| Payor category | Commercial | 0.019 | 0.075 |
| | Medicare/Medicaid | -0.075 | -0.083 |
| | Self/Other | 0.084 | 0.034 |
| Elixhauser score | | -0.131 | -0.005 |
| Severity of Illness | Minor | 0.035 | -0.020 |
| | Moderate | -0.042 | 0.029 |
| | Major | -0.062 | -0.011 |
| | Extreme | -0.062 | -0.000 |
| Procedure Type | Non-Elective | -0.004 | 0.006 |
| Hospital Location | Urban | 0.101 | 0.000 |
| Hospital Type | Teaching | -0.183 | 0.028 |
| Hospital Bed Size | 1-299 | -0.140 | -0.000 |
| | 300-499 | 0.594 | -0.036 |
| | 500 | -0.473 | 0.034 |
| Provider Region | Midwest | -0.109 | 0.017 |
| | Northeast | -0.458 | -0.013 |
| | South | 0.194 | -0.038 |
| | West | 0.335 | 0.055 |

*-0.25 < SMD < 0.25 indicates a balanced covariate
Pre-match, a total of 1072 patents met all inclusion and exclusion criteria.
A total of 463 patients were matched for outcome analysis (Group 1, $N$=130; Group 2, $N$=333).

Fig. 4

|  |  | t-test | GEE Model | | |
|---|---|---|---|---|---|
|  | Bivariate comparison Group 1 vs. Group 2 ($SD_{Group1}$ vs. $SD_{Group2}$) | p-value | Odds ratio | 95% CI | p-value |
| Total Mean Index Admission Cost | $36,798 vs. $40,988 ($38,972) vs. ($33,711) | 0.251 | 0.90 | 0.73 – 1.10 | 0.300 |
| Mean Supply Cost for Index Admission | $13,281 vs. $16,371 ($12,320) vs. ($13,841) | 0.027 | 0.81 | 0.68 – 0.98 | 0.026 |
| Length of Stay | 4.05 vs. 4.06 (7.51) vs. (6.00) | 0.993 | 1.00 | 0.70-1.42 | 0.991 |

A total of 463 patients were matched for outcome analysis (Group 1, $N$=130; Group 2, $N$=333). Bivariate data are reported as the mean and standard deviation. Statistical significance is indicated in bold.

Fig. 5

| Average Selling Price (Year 2020) | | |
|---|---|---|
| Microcatheter | Apollo™ detachable tip microcatheter | $1,946 |
| | Marathon™ microcatheter | $757 |
| | Prowler 10 microcatheter | $924 |
| | Scepter XC™ balloon microcatheter | $1,504 |
| | Eclipse balloon microcatheter | $1,797 |
| Liquid Embolic Agent | n-BCA kit | $3,657 |
| | EVOH 18 LES kit | $2,620 |
| | EVOH 34 LES kit | $2,515 |
| Procedure Time Cost (per hour in 2020) | Angiography suite | $642.50 |
| Procedure Time Cost (per hour in 2021*) | | $647.81 |

*Study results calculated based on 2021 procedure costs to reflect most current data available.

Fig. 6

| Technique | Composition per Pedicle | Microcatheter |
|---|---|---|
| n-BCA - microcatheter | 1 unit n-BCA with dilution of 3 mL ethiodized oil: 1 mL n-BCA | 1 Prowler®10 |
| EVOH – Balloon microcatheter | 2 units EVOH 18 | 1 Scepter-XC™ Balloon Microcatheter |
| EVOH – Detachable-tip microcatheter | 2 units EVOH 18, 2 units EVOH 34 | 1 Apollo™ Microcatheter |
| EVOH – Plug and push | 2 units EVOH 18, 2 units EVOH 34 | 1 Marathon™ Microcatheter |

Fig. 7

| Technique | Number of Pedicles | Cost of Liquid Embolic Agent | | Cost of Microcatheter | Cost of Angiography Suite Time (2021 $) |
|---|---|---|---|---|---|
| n-BCA – microcatheter | | n-BCA (3:1) | | Prowler 10 | |
| | 1 | $3,657 | | $924 | $1,360 |
| | 2 | $3,657 | | $1,848 | $1,360 |
| | 3 | $3,657 | | $2,772 | $2,721 |
| | 4 | $3,657 | | $3,696 | $2,721 |
| EVOH – Balloon microcatheter | | EVOH 18 | EVOH 34 | Marathon™ | |
| | 1 | $5,240 | $5,030 | $757 | $1,684 |
| | 2 | $10,480 | $10,060 | $1,514 | $1,684 |
| | 3 | $15,720 | $15,090 | $2,271 | $3,369 |
| | 4 | $20,960 | $20,120 | $3,028 | $3,369 |
| EVOH – Detachable-tip microcatheter | | EVOH 18 | EVOH 34 | Apollo™ | |
| | 1 | $5,240 | $5,030 | $1,946 | $1,684 |
| | 2 | $10,480 | $10,060 | $3,892 | $1,684 |
| | 3 | $15,720 | $15,090 | $5,838 | $3,369 |
| | 4 | $20,960 | $20,120 | $7,784 | $3,369 |
| EVOH – Plug and push | | EVOH 18 | | Scepter XC™ | |
| | 1 | $5,240 | | $1,504 | $1,684 |
| | 2 | $10,480 | | $3,008 | $1,684 |
| | 3 | $15,720 | | $4,512 | $3,369 |
| | 4 | $20,960 | | $6,016 | $3,369 |

*Prices based on CY 2020 Average Sales Price, sourced by data on file

Fig. 8

| Technique | Number of Pedicles | Total Cost | $ Difference from nBCA | Times greater than n-BCA | % Difference from nBCA |
|---|---|---|---|---|---|
| n-BCA – microcatheter | 1 | $5,941 | - | - | - |
| | 2 | $6,865 | - | - | - |
| | 3 | $9,150 | - | - | - |
| | 4 | $10,074 | - | - | - |
| EVOH – Balloon microcatheter | 1 | $8,428 | $2,487 | 1.42 | 30% |
| | 2 | $15,172 | $8,307 | 2.21 | 55% |
| | 3 | $23,601 | $14,451 | 2.58 | 61% |
| | 4 | $30,345 | $20,271 | 3.01 | 67% |
| EVOH – Detachable-tip microcatheter | 1 | $13,900 | $7,959 | 2.34 | 57% |
| | 2 | $26,116 | $19,251 | 3.80 | 74% |
| | 3 | $40,017 | $30,867 | 4.37 | 77% |
| | 4 | $52,233 | $42,159 | 5.18 | 81% |
| EVOH – Plug and push | 1 | $12,711 | $6,770 | 2.14 | 53% |
| | 2 | $23,738 | $16,873 | 3.46 | 71% |
| | 3 | $36,450 | $27,300 | 3.98 | 75% |
| | 4 | $47,477 | $37,403 | 4.71 | 79% |

Fig. 9

| Technique | Number of Pedicles | 12 Cases per year | 52 Cases per year |
|---|---|---|---|
| n-BCA – microcatheter | 1 | $71,297 | $308,953 |
| | 2 | $82,385 | $357,001 |
| | 3 | $109,798 | $475,790 |
| | 4 | $120,886 | $523,838 |
| EVOH – Balloon microcatheter | 1 | $101,140 | $438,272 |
| | 2 | $182,068 | $788,960 |
| | 3 | $283,207 | $1,227,232 |
| | 4 | $364,135 | $1,577,920 |
| EVOH – Detachable-tip microcatheter | 1 | $166,804 | $722,816 |
| | 2 | $313,396 | $1,358,048 |
| | 3 | $480,199 | $2,080,864 |
| | 4 | $626,791 | $2,716,096 |
| EVOH – Plug and push | 1 | $152,536 | $660,988 |
| | 2 | $284,860 | $1,234,392 |
| | 3 | $437,395 | $1,895,380 |
| | 4 | $569,719 | $2,468,784 |

--- delivering, by a first microcatheter, a first embolic agent kit comprising N-butyl cyanoacrylate (n-BCA) within at least one blood vessel adjacent a vascular tangle of a plurality of human patients in a first group
1110

↓ achieving, by the n-BCA kit and the first microcatheter, approximately 30% reduction in preoperative embolization procedure cost for treating at least one blood vessels adjacent a vascular tangle versus a second group treated by an EVOH kit and a balloon microcatheter
1120

↓ achieving, by the n-BCA kit and the first microcatheter, approximately 67% reduction in preoperative embolization procedure cost for treating at least four blood vessels adjacent a vascular tangle versus a second group treated by an EVOH kit and a balloon microcatheter
1130

```
delivering, by a first microcatheter, a first embolic agent kit
comprising N-butyl cyanoacrylate (n-BCA) within at least one blood
vessel adjacent a vascular tangle of a plurality of human patients in a
first group
1210
```

↓

```
achieving, by the n-BCA kit and the first microcatheter,
approximately 57% reduction in preoperative embolization
procedure cost for treating at least one blood vessels adjacent a
vascular tangle versus a second group treated by an EVOH kit and a
detachable-tip microcatheter
1220
```

↓

```
achieving, by the n-BCA kit and the first microcatheter,
approximately 81% reduction in preoperative embolization
procedure cost for treating at least four blood vessels adjacent a
vascular tangle versus a second group treated by an EVOH kit and a
detachable-tip microcatheter
1230
```

```
delivering, by a first microcatheter, a first embolic agent kit
comprising N-butyl cyanoacrylate (n-BCA) within at least one blood
vessel adjacent a vascular tangle of a plurality of human patients in a
first group
1310
          │
          ▼
achieving, by the n-BCA kit and the first microcatheter,
approximately 53% reduction in preoperative embolization
procedure cost for treating at least one blood vessels adjacent a
vascular tangle versus a second group treated by an EVOH kit and a
plug and push microcatheter
1320
          │
          ▼
achieving, by the n-BCA kit and the first microcatheter,
approximately 79% reduction in preoperative embolization
procedure cost for treating at least four blood vessels adjacent a
vascular tangle versus a second group treated by an EVOH kit and a
plug and push microcatheter
1330
```

Fig. 13

1400 delivering, by a first microcatheter, a first embolic agent kit comprising N-butyl cyanoacrylate (the "n-BCA kit") within at least one blood vessel adjacent a vascular tangle of a first plurality of human patients in a first group
1410 reducing a total cost of preoperative embolization procedure in the first group compared to a second group treated by delivering, by a balloon microcatheter, a second embolic agent kit comprising ethylene vinyl alcohol copolymer ("EVOH kit") within at least one blood vessel adjacent a vascular tangle
1420 reducing the total cost of preoperative embolization procedure by $2,487 per preoperative embolization procedure for the first group compared to the second group.
1430

Fig. 14

1500 delivering, by a first microcatheter, a first embolic agent kit comprising N-butyl cyanoacrylate (the "n-BCA kit") within at least one blood vessel adjacent a vascular tangle of a first plurality of human patients in a first group
1510 reducing a total cost of preoperative embolization procedure in the first group compared to a second group treated by delivering, by a detachable-tip microcatheter, a second embolic agent kit comprising ethylene vinyl alcohol copolymer ("EVOH kit") within at least one blood vessel adjacent a vascular tangle
1520 reducing the total cost of preoperative embolization procedure by $7,959 per preoperative embolization procedure for the first group compared to the second group.
1530

Fig. 15

1600 delivering, by a first microcatheter, a first embolic agent kit comprising N-butyl cyanoacrylate (the "n-BCA kit") within at least one blood vessel adjacent a vascular tangle of a first plurality of human patients in a first group
1610 reducing a total cost of preoperative embolization procedure in the first group compared to a second group treated by delivering, by a plug and push, a second embolic agent kit comprising ethylene vinyl alcohol copolymer ("EVOH kit") within at least one blood vessel adjacent a vascular tangle
1620 reducing the total cost of preoperative embolization procedure by $6,770 per preoperative embolization procedure for the first group compared to the second group.
1630

| reducing a total cost of preoperative embolization procedure for a plurality of human patients by delivering, by a first microcatheter, a first embolic agent kit comprising N-butyl cyanoacrylate (the "n-BCA kit") within at least one blood vessel adjacent a vascular tangle of each of the first plurality of human patients.
1710 |
|---|

Fig. 17

SYSTEMS AND METHODS FOR EMBOLIZATION PROCEDURES FOR TREATMENT OF DEFECTS IN THE VASCULATURE

FIELD

This disclosure relates generally to devices for interventional therapeutic treatment or preoperative embolization procedures for treatment of defects in the vasculature.

BACKGROUND

Brain arteriovenous malformations (bAVMs) are uncommon vascular lesions characterized by direct arterial to venous connections, without intermediate capillaries, that form tangled vessels. Brain AVMs are associated with significant patient morbidity and may present with headaches, seizures, spontaneous intracranial hemorrhage, visual disturbances, and progressive neurological deficits. Ruptured AVMs present a hemorrhage risk that is 2-3.7 times higher than risk for unruptured AVMs. The most important objective of surgical removal of the tangled vessels is to reduce the risk of spontaneous bAVM hemorrhage and subsequent morbidity and mortality. Brain AVMs, similar to intranidal aneurysms, may be located deep within the brain, or present large sizes or volumes, precluding treatment with surgery alone. Because intracranial hemorrhages from bAVMs may lead to severe and permanent neurologic deficits, or death, pre-surgical endovascular embolization techniques can reduce risks of hemorrhages and reduce intraoperative bleeding. Several liquid embolic agents are currently available that may reduce the flow to and size of the bAVM through occlusion of the vessels that supply and make up the tangled vessels of the bAVM. Two liquid embolic agents commonly used to achieve presurgical bAVM devascularization are N-butyl cyanoacrylate (n-BCA) and ethylene vinyl alcohol copolymer (EVOH). EVOH and n-BCA have different properties and mechanisms of action. Given the unique properties of the embolic agents, different microcatheters and techniques are tailored for delivering n-BCA and EVOH. Few studies have compared n-BCA and EVOH for vascular tangle volume reduction, complete bAVM occlusion, procedure duration, fluoroscopic imaging duration, blood loss, and complication outcomes. The two liquid embolic agents have similar efficacy and have similar levels of blood loss during surgical bAVM removal. Yet, only one comparative study reported procedure duration outcomes. No other studies have compared economic analysis and cost outcomes among patients treated with n-BCA and EVOH bAVM embolization and the procedure-related costs, including ancillary device costs (for microcatheters) and procedure time-related costs. The solution of this disclosure resolves these and other issues of the art.

SUMMARY

The subject of this disclosure includes methods or uses of liquid embolic agents to treat brain arteriovenous malformations in the neurovascular arteries and veins as well as other vascular beds.

In some examples, the method or use can include delivering a first embolic agent kit having N-butyl cyanoacrylate (the "n-BCA kit") within at least one blood vessel adjacent a vascular tangle in a plurality of human patients in a first group and reducing supply costs of embolization by at least approximately 18%, the odds being determined by a Generalized estimating equations (GEE) model.

In some examples, the first plurality of human patients can include at least approximately 1,072 human patients from a plurality of different hospital sites, with inclusion criteria defined as patients who underwent a preoperative embolization procedure for unruptured brain arteriovenous malformation between 2010-2020 and were identified from the Premier Healthcare Database. Inclusion criteria can also be defined as patients ≥18 years old at the time of index hospital admission.

In some examples for the first plurality of human patients, exclusion criteria can be defined as patients who had their index preoperative embolization procedure by delivering the embolic agent kit comprising n-BCA in combination with an embolic agent kit comprising ethylene vinyl alcohol copolymer ("EVOH").

In some examples, the method or use can include reducing costs of preoperative embolization procedure by delivering, by a first microcatheter, a first embolic agent kit comprising N-butyl cyanoacrylate (the "n-BCA kit") within at least one blood vessel adjacent a vascular tangle in a plurality of human patients in a first group.

In some examples, reducing costs of preoperative embolization procedure by delivering the n-BCA kit can be compared to a second group of the plurality of human patients treated by delivering a second embolic agent kit comprising ethylene vinyl alcohol copolymer (the "EVOH kit") within the at least one blood vessel adjacent the vascular tangle. The second group of the plurality of human patients can be treated by delivering, by a second microcatheter, the EVOH kit within the least one blood vessel adjacent the vascular tangle. The cost of preoperative embolization procedure can be at least approximately 30% lower for the first group versus the second group.

In some examples, the second group of the plurality of human patients can be treated by delivering, by a third microcatheter, the EVOH kit within the least one blood vessel adjacent the vascular tangle. The cost of preoperative embolization procedure can be at least approximately 57% lower for the first group versus the second group.

In some examples, the second group of the plurality of human patients can be treated by delivering, by a fourth microcatheter, the EVOH kit within the least one blood vessel adjacent the vascular tangle. The cost of preoperative embolization procedure can be at least approximately 53% lower for the first group versus the second group.

In some examples, the method or use can further include achieving, by the n-BCA kit and the first microcatheter, approximately 67% lower preoperative embolization procedure cost for treating at least four blood vessels adjacent a vascular tangle versus a second group treated by an EVOH kit and a second microcatheter.

In some examples, the method or use can further include achieving, by the n-BCA kit and the first microcatheter, approximately 81% lower preoperative embolization procedure cost for treating at least four blood vessels adjacent a vascular tangle versus a second group treated by an EVOH kit and a third microcatheter.

In some examples, the method or use can further include achieving, by the n-BCA kit and the first microcatheter, approximately 79% lower preoperative embolization procedure cost for treating at least four blood vessels adjacent a vascular tangle versus a second group treated by an EVOH kit and a fourth microcatheter.

In some examples, the cost of the first embolic agent can be at least approximately 30% lower versus the cost of the second embolic agent.

In some examples, the method or use can further include delivering the EVOH kit by a balloon microcatheter to the second group and achieving at least approximately 30% reduced cost for the first group versus the second group.

In some examples, the method or use can further include delivering the EVOH kit by a detachable-tip microcatheter to the second group and achieving at least approximately 57% reduced cost for the first group versus the second group.

In some examples, the method or use can further include delivering the EVOH kit by a plug and push microcatheter to the second group and achieving at least approximately 53% reduced cost for the first group versus the second group.

In some examples, a method or use described herein can include reducing a total cost of preoperative embolization procedure in a first plurality of human patients in a first group by delivering, by a first microcatheter, a first embolic agent kit comprising N-butyl cyanoacrylate (the "n-BCA kit") within at least one blood vessel adjacent a vascular tangle of each of the first plurality of human patients.

In some examples, the method or use can further include reducing the total cost of preoperative embolization procedure by at least approximately $2,487 compared to a second group treated by delivering, by a balloon microcatheter, a second embolic agent kit comprising ethylene vinyl alcohol copolymer (the "EVOH kit") within at least one blood vessel adjacent a vascular tangle. The total cost of preoperative embolization procedure can be adjusted for medical inflation and reported in 2020 US dollars ($).

In some examples, the method or use can further include reducing the total cost of preoperative embolization procedure by at least approximately $7,959 compared to a second group treated by delivering, by a detachable-tip microcatheter, a second embolic agent kit comprising ethylene vinyl alcohol copolymer (the "EVOH kit") within at least one blood vessel adjacent a vascular tangle. The total cost of preoperative embolization procedure can be adjusted for medical inflation and reported in 2020 US dollars ($).

In some examples, the method or use can further include reducing the total cost of preoperative embolization procedure by at least approximately $6,770 compared to a second group treated by delivering, by a plug and push microcatheter, a second embolic agent kit comprising ethylene vinyl alcohol copolymer (the "EVOH kit") within at least one blood vessel adjacent a vascular tangle. The total cost of preoperative embolization procedure can be adjusted for medical inflation and reported in 2020 US dollars ($).

In some examples, a method or use can include delivering a first embolic agent kit comprising a first microcatheter and N-butyl cyanoacrylate (the "n-BCA kit") within at least one blood vessel adjacent a vascular tangle of a plurality of human patients and reducing costs of preoperative embolization procedure from approximately 30% to approximately 57%, by the n-BCA kit.

In some examples, the method or use can further include achieving at least approximately 30% reduced cost versus delivering a second embolic kit comprising a balloon microcatheter and ethylene vinyl alcohol copolymer (the "EVOH kit").

In some examples, the method or use can further include achieving at least approximately 57% reduced cost versus delivering a second embolic kit comprising a detachable-tip microcatheter and ethylene vinyl alcohol copolymer (the "EVOH kit").

In some examples, the method or use can further include achieving at least approximately 53% reduced cost versus delivering a second embolic kit comprising a plug and push microcatheter and ethylene vinyl alcohol copolymer (the "EVOH kit").

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 2-3 show tables summarizing characteristics of the study population in pre- and post-match cohorts.

FIG. 4 is a table summarizing mean differences before and after matching in the primary outcome cohort.

FIG. 5 is a table summarizing total index admission cost, supply cost, and length of stay between groups of the study.

FIG. 6 is a table summarizing average selling price of supply costs and procedure time costs in the study of this disclosure.

FIG. 7 is a table summarizing liquid embolic agent composition by technique and microcatheter used in the study of this disclosure.

FIG. 8 is a table summarizing per procedure cost analysis by technique and number of pedicles embolized according to the study of this disclosure.

FIG. 9 is a table summarizing per procedure total cost analysis results by technique and number of pedicles embolized according to the study of this disclosure.

FIG. 10 is a table summarizing cohort 12-cases per year and 52-cases per year cost analysis results by technique and number of pedicles embolized according to the study of this disclosure.

FIG. 11 depicts a graphical overview of a method of treating an aneurysm according to this disclosure.

FIG. 12 depicts a graphical overview of a method of treating an aneurysm according to this disclosure.

FIG. 13 depicts a graphical overview of a method of treating an aneurysm according to this disclosure.

FIG. 14 depicts a graphical overview of a method of treating an aneurysm according to this disclosure.

FIG. 15 depicts a graphical overview of a method of treating an aneurysm according to this disclosure.

FIG. 16 depicts a graphical overview of a method of treating an aneurysm according to this disclosure.

FIG. 17 depicts a graphical overview of a method of treating an aneurysm according to this disclosure.

DETAILED DESCRIPTION

Figure 1:
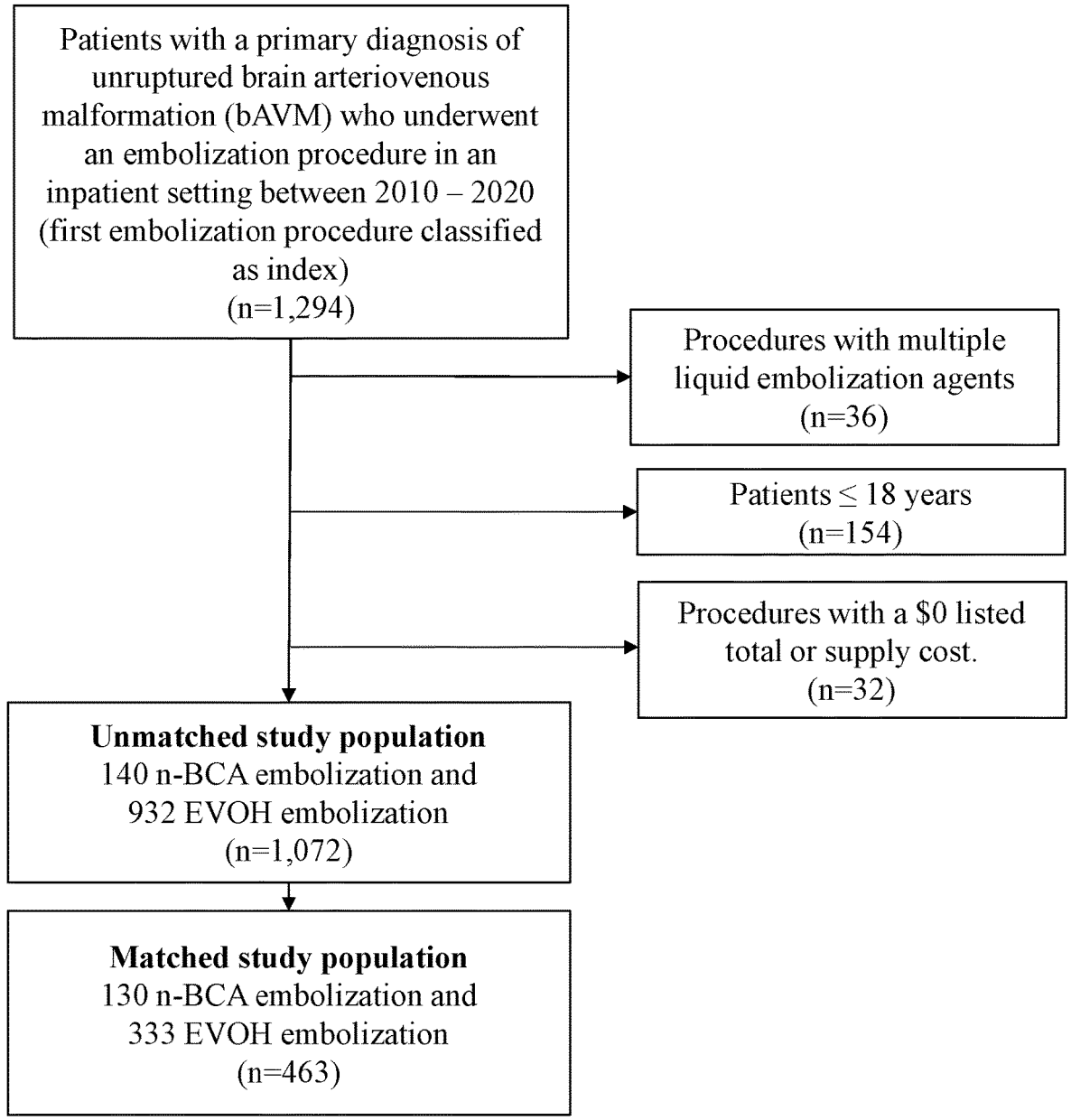
FIG. 1 is a flow diagram illustrating flow of enrollment in the study of this disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited to, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient.

As discussed herein, "operator" may include a doctor, surgeon, or any other individual, medical interventionalist, or delivery instrumentation associated with delivery of a flow diverter device, and related instrumentation, to an aneurysm in the vasculature of a subject.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist.

As discussed herein, the term "rate" as used throughout this disclosure is intended to refer to the rate for a particular population of patients according to a particular investigation rather than information or levels related to a single patient. However, herein the term "rate" and "level" can be used interchangeably. In any study, single patient levels are used to determine "rates." Any one patient's level may be the notable point in a reported rate.

As used herein, the terms "about" or "approximately" for any numerical values or ranges indicate a suitable tolerance. More specifically, "about" or "approximately" can refer to the range of values ±20% of the recited value, e.g. "about 90%" can refer to the range of values from 71% to 99%.

As discussed herein, the term "safety", as it relates to a liquid embolic agent, preoperative embolization, method of treatment, or medical device refers to a relatively low severity of adverse events, including spontaneous bAVM hemorrhage or neurological deficit. Spontaneous bAVM hemorrhage events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration (FDA), EMEA or a corresponding national regulatory agency. For example, a clinical study may be an adequately sized, randomized, double-blinded controlled study used to clinically prove the effects of the liquid embolic systems and related systems of the disclosure. Most preferably to clinically prove the effects of the system with respect to a brain AVM, for example, to achieve a clinically effective outcome for the patient with the brain AVM features (e.g., intranidal aneurysms, deep or eloquent location, or large size/volume) and/or achieve reduced size of large brain AVMs and make surgical removal more feasible on the subject to treatment.

As discussed herein, the term "computed tomography" or "CT" means one or more scans that make use of computer-processed combinations of two or more X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

The present disclosure is related to systems, methods, and devices for treating arteriovenous malformations (AVMs) and restoring perfusion in blood vessels. Efficacy, safety, and economic outcomes between liquid embolic agents for the treatment of brain AVMs were compared.

Study Overview

This disclosure is more clearly understood with a corresponding study discussed more particularly below with respect to treatment of brain arteriovenous malformations, attached hereto in Appendix 1, and incorporated by reference in its entirety as if set forth verbatim herein. It is understood that data is presented herein for purposes of illustration and should not be construed as limiting the scope of the disclosed technology in any way or excluding any alternative or additional embodiments.

A primary objective of the study was to compare the economic outcomes among human patients undergoing brain arteriovenous malformations (bAVM) with liquid embolic agents, which can include n-butyl cyanoacrylate (n-BCA; TRUFILL Liquid Embolic System, CERENOVUS, Irvine, Calif.), an adhesive polymer that is diluted with ethiodized oil mixed with tantalum powder. The n-BCA polymerizes into a solid, radiopaque, thrombogenic material upon contact with bodily fluids and tissue, thereby preventing blood flow through the embolized bAVM pedicle. The n-BCA solution can be diluted with ethiodized oil to tailor the polymerization rate and achieve the desired viscosity based on the clinical characteristics of the patient and their bAVM. The economic outcomes were compared with those of ethylene vinyl alcohol copolymer (EVOH; Onyx Liquid Embolic System, Medtronic, Minneapolis, Minn.), a non-adhesive liquid that precipitates out of the dimethyl sulfoxide (DMSO) tantalum powder solution used to deliver the EVOH to the cannulated AVM pedicle. After precipitation, EVOH forms a minimally thrombogenic, radiopaque, spongy cast that prevents blood flow through the embolized bAVM pedicle. EVOH comes in two concentrations with corresponding precipitation rates and cannot be mixed. The difference in concentration and polymerization rates require deployment technique and required equipment to be tailored to the bAVM and the chosen liquid embolic agent, all of which could potentially lead to differences in procedure-related costs (including liquid embolic agent and ancillary device costs) and procedure time-related economic outcomes.

Though previous studies have provided useful information on the comparisons between n-BCA and EVOH for presurgical brain AVM devascularization, the generalizability of their findings have been limited to either intermediate efficacy outcomes, such as percentage of patients with complete nidal occlusion, or brain AVM volume reduction. See Raymond J, et al. (2005) *Embolization as one modality in a combined strategy for the management of cerebral arteriovenous malformations. Interv Neuroradiol* 11 (Suppl 1): 57-62; see also Saatci I, et al. (2011) *Endovascular treatment of brain arteriovenous malformations with prolonged intranidal Onyx injection technique: long-term results in 350 consecutive patients with completed endovascular treatment course. J Neurosurg* 115 (1): 78-88; see also Lv X, et al. (2012) *Hemorrhage risk after partial endovascular NBCA and ONYX embolization for brain arteriovenous malformation. Neurol Res* 34 (6): 552-556; see also Dalyai R, et al. (2014) *Smoking is a negative predictor of arteriovenous malformation posttreatment obliteration: analysis of vascular risk factors in 774 patients. Neurosurg Focus* 37 (3): E3; see also Velat G J, et al. (2008) *Comparison of N-butyl cyanoacrylate and onyx for the embolization of intracranial arteriovenous malformations: analysis of fluoroscopy and procedure times. Neurosurgery* 63 (1 Suppl 1): ONS73-78; see also Loh Y, et al. (2010) *A prospective, multicenter, randomized trial of the Onyx liquid embolic system and N-butyl cyanoacrylate embolization of cerebral arteriovenous malformations. Clinical article. J Neurosurg* 113 (4): 733-741; see also Lv X, et al. (2011) *Complication risk of endovascular embolization for cerebral arteriovenous malformation. Eur J Radiol* 80 (3): 776-779. These previous studies did not examine the rates of hemorrhage during surgical removal of the bAVMs to provide evidence for which liquid embolic agent is more efficacious at preventing hemorrhage and because the degree of occlusion does not necessarily correlate with the ease of bAVM surgical removal or how likely bAVMs are to exhibit an intraoperative hemorrhage, the comparative value of these intermediate endpoints is limited.

To resolve the limitation, a first study utilized a nationally representative hospital billing dataset to perform a retrospective cohort analysis of hospital-level data from the Premier Healthcare Database (PHD) for procedural costs comparing total supply costs for bAVM embolization in terms of real-world clinical and economic outcomes. In particular, the first study validated findings that supply costs, including liquid embolic agent and procedure time when using n-BCA are lower than for patients treated with EVOH, as described in greater detail below. The PHD contains complete clinical coding, hospital cost, and patient billing data from more than 600 hospitals throughout the United States. Premier collects data from participating hospitals in its health care alliance. The Premier health care alliance was formed for hospitals to share knowledge, improve patient safety, and reduce risks.

In a second study, based on the validated findings of the retrospective cohort analysis, an economic model was developed comparing procedural costs of four brain AVM embolization techniques including n-BCA with a Prowler microcatheter, EVOH with "plug and push" technique (with any microcatheter), EVOH with a detachable-tip microcatheter, and EVOH with a balloon microcatheter, which are described in greater detail below. Because brain AVMs that require presurgical embolization may be highly variable in size and volume (e.g., from about 0.08 $cm^3$ to about 290 $cm^3$), the second study standardized the analysis by considering embolization on a per pedicle basis rather than comparing liquid embolic agents in a volume-to-volume manner. Factors that may require increased amounts of liquid embolic agents can include vessel size, vessel length, or microcatheter used during the procedure. Accordingly, the second study included the total number of liquid embolic agent kits required to embolize one to four pedicles per patient for the four brain AVM embolization techniques.

All brain AVMs treated were assumed to be similar in size and volume. The number of pedicle and total number of liquid embolic agent kits, including type and number of microcatheter required, are shown in FIG. 6.

All study variables are summarized as the mean and standard deviation for continuous variables and the frequency and percentage for categorical variables. Bivariate statistical tests (Chi square tests for categorical variables and t-tests for continuous variable comparison) were conducted to examine and describe between-group differences in potential confounding factors such as patient characteristics (e.g., age, gender, race), procedure characteristics (e.g., payor, elective, non-elective), provider characteristics (e.g., teaching status, geographical location, bed size), patient severity of illness, and patient co-morbid conditions.

Results of the First Study

As shown in FIG. 1, the retrospective cohort included 1,072 patients aged 18 years and above who had undergone preoperative embolization procedure with a primary diagnosis of unruptured bAVMs from inpatient admissions between Jan. 1, 2010 to Jun. 30, 2020 (140 Group 1 (n-BCA) and 932 Group 2 (EVOH)). Pre-match, the age mean was 47.06±15.75 for Group 1 and 46.80±16.65 for Group 2. Post-match, the age mean for Group 1 was 47.51±15.60 and 45.97±16.15 for Group 2. In this cohort, Group 1 and Group 2 differed in terms of hospital bed size (1-299 beds: 6.4% vs. 10.3%; 300-499 beds: 44.3% vs. 17.9%; 500 beds: 49.3% vs. 71.8%, p<0.001) and provider region (midwest: 7.9% vs. 11.1%; northeast 10.7% vs. 28.4%; south: 62.1% vs. 52.6%; west: 19.3% vs. 7.9%, p<0.001), but conformed in terms of age, gender, race/ethnicity, insurance type, elective or emergent procedure, payor status, hospital type, and all patient refined diagnosis related groups (APT-DRG).

A summary of the characteristics of the study population are provided in FIGS. 2 and 3. Of the 463 patients matched for outcome analysis in the study that were treated with n-BCA (group 1) or EVOH (group 2), the mean age for patients was 47.65±15.54 or 46.65±16.25 years, respectively (standard mean difference ("SMD")=0.063 post-match). Additionally, just under half of the patients were male (43.8% group 1; 47.4% group 2; SMD=−0.023). Over half of the patients were white in both groups (61.5% group 1; 60.7% group 2; SMD=0.032) with the remaining patients being classified as African American (16.9% group 1; 18.6% group 2; SMD=−0.054) or Other (21.5% group 1; 20.7% group 2; SMD=0.009). The majority of patients were enrolled in Medicare or Medicaid (79.2% group 1; 76.6% group 2; SMD=0.044), with 11.5% in group 1 and 12.6% in group 2 (SMD=−0.016) having commercial coverage, and 9.2% in group 1 and 10.8% in group 2 (SMD=−0.044) having self or other coverage. Patient severity of illness was categorized by control for diagnosis related groups (DRGs). The majority of patients (63.8% in group 1 and 66.7% in group 2; SMD=−0.082) fell within DRG #027 for craniotomy and endovascular intracranial procedures without complication or comorbidity (CC)/major complication or comorbidity (MCC) For DRG #026 for craniotomy and endovascular intracranial procedures with complication or comorbidity (CC), 14.6% were identified in group 1 and 15.0% in group 2 (SMD=0.003). For DRG #025 for craniotomy and endovascular intracranial procedures with major complication or comorbidity (MCC), 18.5% were identified in group 1 and 17.1% in group 2 (SMD=0.060). The remaining patients (2.3% group 1; 0.6% group 2; SMD=0.093) were either in DRG #003 for ECMO or tracheostomy with MV >96 hours or PDX except face, mouth and neck with major O.R. procedure, or DRG classification of "other" (0.8% group 1; 0.6% group 2; SMD=0.021). In both groups, very few patients had the AVM surgically resected during the index procedure (6.9% group 1; 5.7% group 1; SMD=0.084). Patients had an Elixhauser Score mean of 1.42±1.43 in group 1 and 1.39±1.28 for group 2 (SMD=0.024).

The results of propensity matching are detailed in FIG. 4. A total of 480 patients were propensity matched for outcome comparison. In general, standardized mean difference (SMD) between −0.25 and 0.25 indicate balanced covariates. Examination of SMDs revealed a perfect balance of covariates among the matched cohort, with no significant differences observed for any of the covariates. Examination of SMDs for the matched cohort depicted a good balance. Accordingly, no covariate was adjusted for the GEE model regression analysis comparing embolic agents and costs of care.

Bivariate and adjusted analyses of average cost for pre-operative embolization admission using n-BCA and EVOH were conducted on the propensity-matched cohort (n=463, 130 n-BCA/333 EVOH) to compare Group 1 and Group 2. Total cost for preoperative embolization admission in patients using n-BCA was lower than the average total cost in patients using EVOH (Group 1 vs. Group 2, $36,798 [Standard Deviation ("SD") $38,972] vs. $40,988 [SD $33,711], p=0.251) but did not emerge to be a statistically significantly difference in GEE analysis (adjusted ratio of the mean 0.90, 95% Confidence Interval ("CI") 0.73-1.10, p=0.300). In contrast, there was a significant difference in supply cost between n-BCA and EVOH (Group 1 vs. Group 2, $13,281 [SD $12,320] vs. $16,371 [SD $13,841], p=0.027). The GEE model showed consistent results in supply cost between n-BCA and EVOH (adjusted ratio of the mean 0.81, 95% CI 0.68-0.98, p=0.026). No significant difference was found in length of stay between patients using n-BCA and EVOH (Group 1 vs. Group 2, 4.05 [SD=7.51] vs. 4.06 [SD=6.0], p from bivariate analysis=0.993 and p from GEE=0.991). The cost and length of stay in patients using n-BCA and EVOH are shown in the table of FIG. 5.

While length of stay and total hospital duration were similar between patients with bAVMs treated using n-BCA and EVOH, patients treated using n-BCA had significantly lower supply cost than patients treated with EVOH for preoperative embolization. Additionally, The average total cost for preoperative embolization admission in patients using n-BCA was lower than the total cost in patients using EVOH, in general, but were not statistically significant when using the Premier database. The type of technique used when treating patients with EVOH is not identifiable in the Premier database. Accordingly, by assessing the three different techniques and the supplies (e.g., amount of liquid embolic agent, type, and number of microcatheters, and procedure time), the total cost difference between treating patients with n-BCA and EVOH can be estimated.

Results of the Second Study

The most common vascular access site for brain AVMs is the femoral artery. For each of the four brain AVM technique analyzed in this cost consequence study, the data used the microcatheter specific for femoral artery entry to the target bAVM pedicle.

For the n-BCA technique, the primary analysis assumed a 3:1 mixture of ethiodized oil mixed with tantalum powder and n-BCA. In the scenario analyses, an alternative dilution of 2:1 ethiodized oil to n-BCA was assumed. An n-BCA kit (Cerenovus, Irvine, Calif.) containing a 10 mL vial of ethiodized oil, 1 g of tantalum powder, and 1 mL of n-BCA, was used to prepare 4 mL of the 3:1 dilution. For the cost comparison study, a maximum of 8 mL of liquid embolic agent mixture was assumed to be required if up to 2 mL were used to embolize each pedicle. After cannulating the target pedicle, up to 0.5 mL of n-BCA was injected to embolize it, then a branch run angiogram was performed to visualize the embolized pedicle. Once sufficient pedicle embolization was confirmed, the microcatheter (Prowler 10, Cerenovus) was carefully withdrawn from the bAVM. The Prowler microcatheter was selected as the ancillary device since it is recommended for use with n-BCA.

An Onyx™ EVOH kit (Onyx™ 18 and Onyx™ 34, Medtronic plc, Minneapolis, Minn.) contains 1.5 mL of either Onyx™ 18 (6% EVOH) or Onyx™ 34 (8% EVOH) and 1.5 mL of DMSO. For the EVOH with detachable-tip microcatheter technique, the tip detachment prevents risks associated with the entire microcathether sticking to the EVOH cast embolizing the nidus. See Miller T R, Giacon L, Kole M J, Chen R, Jindal G et al. (2018) *Onyx embolization with the Apollo detachable tip microcatheter: A single-center experience*. Intery Neuroradiol 24 (3): 339-344. In particular, detachable-tip microcatheter (Apollo™, Medtronic plc) was used with two kits of Onyx™ 18 and two kits of Onyx™ 34 per pedicle (see FIG. 7). Once EVOH was injected using a detachable-tip microcatheter and embolization was complete, the microcatheter was gently withdrawn until it either released from the EVOH cast or until the tip detached (See Miller et al., 2018). This feature helped prevent catheter retention where the entire microcatheter would be left in the patient until it is possible to surgically remove the bAVM.

For the balloon microcatheter with EVOH technique, a balloon microcatheter helps prevent reflux of EVOH during the embolization procedure. In particular, balloon microcatheter (Scepter XC™, MicroVention Inc., Aliso Viejo, Calif.) was used with two kits of Onyx™ 18 per pedicle (see FIG. 7). Once the target pedicle was cannulated, the balloon distal to the microcatheter tip was inflated to allow for embolization of the bAVM with EVOH and prevent excess reflux. See Jagadeesan B D, Grande A W, Tummala R P (2018) *Safety and Feasibility of Balloon-Assisted Embolization with Onyx of Brain Arteriovenous Malformations Revisited. Personal Experience with the Scepter XC Balloon Microcatheter*. Intery Neurol 7 (6): 439-444. When the embolization was complete the balloon was deflated and the microcatheter was gently withdrawn until it released from the EVOH cast. See Kim S T, Jeong H W, Seo J (2013) O*nyx Embolization of Dural Arteriovenous Fistula, using Scepter C Balloon Catheter: a Case Report*. Neurointervention 8 (2): 110-114.

For the plug and push technique with EVOH involves slowly injecting a plug of embolic agent in front of the catheter tip and refluxing until the embolic agent reaches the tip of the catheter. For the plug and push technique, two kits of Onyx™ 18 and two kits of Onyx™ 34 were used per pedicle (see FIG. 7). In particular, Onyx™ 18 is used for the push part of the technique and Onyx™ 34 is used as the plug. Once the EVOH refluxes to the catheter, the embolization was paused for 2 min to allow for polymer precipitation, then additional EVOH was injected in small volumes and pushed into the nidus. See Weber W, Kis B, Siekmann R, Kuehne D (2007) *Endovascular Treatment of Intracranial Arteriovenous Malformations with Onyx: Technical Aspects*. American Journal of Neuroradiology 28 (2): 371-377; Siekmann R (2005) *Basics and Principles in the Application of Onyx LD Liquid Embolic System in the Endovascular Treatment of Cerebral Arteriovenous Malformations*. Intery Neuroradiol 11 (Suppl 1): 131-140. The embolization was stopped once there was enough reflux and the cast was attenuated to allow for additional penetration of the bAVM nidus. The microcatheter was removed by gently applying tension which was slowly increased and decreased until the tip detaches from the cast. Use of Marathon™ microcatheters (Medtronic plc) was assumed for the plug and push technique since it is a DMSO-compatible microcatheter that is indicated for neurovascular use.

Procedure Time Analysis

Procedure duration per emolization varies between the four different techniques. For example, procedure duration with n-BCA was 2.1 hours per embolization, with an average of 1.7 pedicles embolized per patient, whereas duration with EVOH was 2.6 hours per embolization, with about 1.8 pedicles embolized per patient. Accordingly, for the 1 or 2 pedicle analyses, the procedure duration input for n-BCA was 2.1 hours and 2.6 hours for EVOH. For a 3 or 4 pedicle procedure, the duration input was assumed to be twice as long, with 4.2 hours for n-BCA and 5.2 hours for EVOH. Variation in procedure duration was examined in the sensitivity analyses described in more detail below.

Hourly cost of angiography suite time was approximately $539 in 2014. See Beheshti M V, Meek J (2014) *Calculation of operating expenses for conventional transarterial chemoembolization in an academic medical center: a step toward defining the value of transarterial chemoembolization*. J Vasc Intery Radiol 25 (4): 567-574. The angiography suite hourly costs included $75.27 for angiography suite direct fixed costs, $290.30 for direct labor costs, $21.24 for indirect overhead facility costs, $73 for indirect hospital overhead and administrative costs, and $79 for college of medicine overhead and administrative costs. The labor costs included amounts for interventional radiology personnel: 1.5 technologists, 1.2 nurses, 0.7 administrative support, 1 faculty, 1 fellow, and 0.35 coordinators per hour. Costs were inflated from 2014 to 2021 US dollars using the medical care component of the CPI index for all urban consumers (US Bureau of Labor Statistics). For example, the hourly cost of angiography suite time was approximately $642.50 in 2020 and inflated to $647 in 2021 (see FIG. 6).

Cost Analysis

Cost analyses were performed for the four different techniques described above. The table in FIG. 6 provides the 2020 average selling price of liquid embolic agents, microcatheters, and procedure time (e.g., angiography suite in cost per hour). Overall, costs of microcatheters having a detachable tip were greater, followed by balloon microcatheters. The liquid embolic agent composition and concentration can be varied based on the microcatheter used. For n-BCA and the Plug-andPush techniques, the Prowler10 and the Marathon™ microcatheters are recommended for their respective liquid embolic instruction for use (IFU). The Apollo™ Detachable-Tip microcatheters were developed for EVOH to prevent catheter retention during preoperative embolization procedures. Sceptor-XC™ is a balloon microcatheter that, when inflated, may help prevent EVOH reflux along the microcatheter. Procedure time costs include angiography suite time and can include labor costs for technicians.

As shown in the table in FIG. 6, the cost of the n-BCA kits are greater than the EVOH kits, however kits can include different concentrations of liquid embolic agents that can be diluted as needed for the particular use, as shown in FIG. 7. For example, a 3:1 dilution of n-BCA can make approximately 4 mL of liquid embolic agent and can provide enough material to embolize up to two pedicles when 2 mL of embolic agent are used on each pedicle. Each EVOH kit include approximately 1.5 mL of liquid embolic and 1.5 mL of dimethyl sulfoxide (DMSO). Volume of EVOH required depends on the microcatheter and delivery technique used. For instance, using the plug-and-push technique can require two units of EVOH 34 and two units of EVOH 18 for a total volume of 9 mL (see FIG. 7).

For each technique, FIG. 8 provides the total number of devices used per pedicle and per procedure. Costs of microcathether and liquid embolic agents used in the analyses were based on annual 2020 average selling prices (ASPs) while the cost of the angiography suite time and procedure time costs were based on annual 2021 average cost.

FIG. 9 shows total per procedure costs for one to four embolized pedicles ranged from $5,941 to $10,074 for the n-BCA technique, $8,428 to $30,345 for the EVOH balloon microcatheter technique, $13,900 to $52,233 for the EVOH detachable-tip microcatheter technique, and $12,711 to $47,477 for the EVOH plug and push technique. Per procedure costs for the three EVOH techniques ranged from 1.42 to 5.18 times the cost of the n-BCA technique (when comparing procedures with the same number of pedicles embolized), indicating that substantial cost savings may be associated with using n-BCA for bAVM embolization rather than EVOH when considering cost of devices and angiography suite time. Microcatheters designed to reduce retention of the entire catheter and prevent EVOH reflux may help avoid these complications, but they are associated with additional costs compared with ancillary devices used with techniques such as n-BCA.

In addition to per procedure analyses, annual cohort analyses were performed to estimate the costs of treating one bAVM case per month for low volume centers (12 total) and one case per week for high volume centers (52 total). FIG. 10 illustrates per procedure and annual cohort analyses for each of the four techniques (n-BCA using a Prowler microcatheter, EVOH with "plug and push" technique and Marathon microcatheter, EVOH with a detachable-tip microcatheter, and EVOH with a balloon microcatheter) considering embolization of one to four pedicles per bAVM per patient. The total number of devices used per-pedical and per procedure were assumed to be 2 mL of liquid embolic agent per pedicle. Overall, costs for the n-BCA technique were lower than all three EVOH techniques for all analyses when comparing costs per procedure (one to four pedicles), and for the low or high-volume annual cohorts. FIG. 10 shows total 12-cases per year costs for one to four embolized pedicles ranged from $71,297 to $120,886 for the n-BCA technique, $101,140 to $364,135 for the EVOH balloon microcatheter technique, $166,804 to $626,791 for the EVOH detachable-tip microcatheter technique, and $152,536 to $569,719 for the EVOH plug and push technique. Total cost for 52-cases per year costs for one to four embolized pedicles ranged from $308,953 to $523,838 for the n-BCA technique, $438,272 to $1,577,920 for the EVOH balloon microcatheter technique, $722,816 to $2,716,096 for the EVOH detachable-tip microcatheter technique, and $660,988 to $2,468,784 for the EVOH plug and push technique.

Embolizing bAVMs with multiple pedicles was associated with increased cost for liquid embolic in all EVOH techniques given that additional kits were required for each pedicle. In contrast, costs for liquid embolic were static for the n-BCA technique since a single n-BCA kit provided adequate volume for multiple pedicles. Additionally increased costs for EVOH procedures compared to n-BCA were driven by use of additional and/or specialized microcatheters required to embolize bAVMs. and more liquid embolic agent per pedicle. For instance, for EVOH technique with the balloon microcatheter, four balloon microcatheters and eight units of EVOH 18 are needed to treat four pedicles. Additionally, for EVOH technique with the detachable tip microcatheter, four Apollo detachable tip microcatheters are required and eight units of EVOH 18 combined with eight units EVOH 34 are needed to treat four pedicles. Further, for EVOH "plug and push" technique, four Marathon microcatheters with eight units of EVOH 18 combined with eight units of EVOH 34 are required. Angiography suite costs were also higher with EVOH techniques because they required additional time to perform embolization procedures compared to n-BCA, although were not a major driver of cost differences.

Sensitivity and Scenario Analysis

Sensitivity analyses were performed to examine the effects of varying categories of input costs by ±20% and using alternate assumptions for the duration of procedure time with the different EVOH techniques. Varying the angiography suite costs by ±20% had the smallest impact of per procedure results, followed by varying the microcatheter costs by ±20%, while varying the liquid embolic agent costs by ±20% had the largest impact on the results. The category cost sensitivity analyses were consistent with the primary analysis and the ranking of techniques from least to most expensive was the same for each analysis performed compared to the primary analysis. Scenario analyses were performed using a 2:1 n-BCA dilution, adding a Prowler 10 microcatheter to the EVOH balloon technique, or using an Eclipse balloon microcatheter instead of a Scepter XC™ balloon microcatheter. Both scenario analyses examining the balloon microcatheter technique demonstrated higher costs than the primary analysis.

Sensitivity analyses varied cost categories by ±20% (all liquid embolic agents, all microcatheters, or angiography suite time costs) and varied procedure duration and angiography suite costs by ±20% (for EVOH). Scenario analyses were performed assuming an alternative dilution of n-BCA (2:1 instead of 3:1), use of additional ancillary devices, or techniques involving alternate resource use. For the EVOH balloon microcatheter technique, scenario analyses were performed on additional resource use by adding the costs of a Prowler 10 microcatheter in addition to a Scepter XC™ balloon microcatheter. An EVOH balloon catheter technique scenario analysis was also performed for use of Eclipse balloon microcatheters (Balt LLC, Irvine, Calif.) rather than Scepter XC™ balloon microcatheters to examine the cor85sts associated with an alternative device. Sensitivity and scenario analyses were performed for the per procedure results only.

In sum, the order of techniques from least to most expensive was n-BCA, followed by EVOH with balloon microcatheters, then EVOH with detachable-tip microcatheters, and EVOH using plug and push. The sensitivity and scenario analysis results were consistent with the primary analysis as the ranking of the techniques from least to most expensive was consistent, and the cost of liquid embolic agents was a key driver. Scenario analyses for balloon microcatheters were associated with higher costs than the base case results due to the use of an additional microcatheter per pedicle (per IFU) or a more costly alternative balloon microcatheter. Group 1 was also associated with less angiography suite costs compared to the comparator group (n-BCA versus EVOH; 2.1 hours versus 2.6 hours, p<0.0001). Embolization with n-BCA procedures required significantly shorter fluoroscopy time (n-BCA versus EVOH; 37 minutes versus 57 minutes, p<0.0001). Extended procedure duration is associated with significantly more (14%) complications for every additional 30 mins of procedure time. These results indicate a potential economic benefit associated with use the embolic agent of Group 1 versus those of Group 2.

FIG. 11 depicts a method or use 1100 and can include 1111 delivering, by a first microcatheter, a first embolic agent kit comprising N-butyl cyanoacrylate (n-BCA) within at least one blood vessel adjacent a vascular tangle of a plurality of human patients in a first group; 1120 achieving, by the n-BCA kit and the first microcatheter, approximately 30% reduction in preoperative embolization procedure cost for treating at least one blood vessels adjacent a vascular tangle versus a second group treated by an EVOH kit and a balloon microcatheter; and 1130 achieving, by the n-BCA kit and the first microcatheter, approximately 67% reduction in preoperative embolization procedure cost for treating at least four blood vessels adjacent a vascular tangle versus a second group treated by an EVOH kit and a balloon microcatheter. Method or use 1100 can end after step 1120 or after step 1130.

In other embodiments, additional steps according to the examples described above can be performed.

FIG. 12 depicts a method or use 1200 and can include 1212 delivering, by a first microcatheter, a first embolic agent kit comprising N-butyl cyanoacrylate (n-BCA) within at least one blood vessel adjacent a vascular tangle of a plurality of human patients in a first group; 1220 achieving, by the n-BCA kit and the first microcatheter, approximately 57% reduction in preoperative embolization procedure cost for treating at least one blood vessels adjacent a vascular tangle versus a second group treated by an EVOH kit and a detachable-tip microcatheter; and 1230 achieving, by the n-BCA kit and the first microcatheter, approximately 81% reduction in preoperative embolization procedure cost for treating at least four blood vessels adjacent a vascular tangle versus a second group treated by an EVOH kit and a detachable-tip microcatheter. Method or use 1200 can end after step 1220 or after step 1230. In other embodiments, additional steps according to the examples described above can be performed.

FIG. 13 depicts a method or use 1300 and can include 1310 delivering, by a first microcatheter, a first embolic agent kit comprising N-butyl cyanoacrylate (n-BCA) within at least one blood vessel adjacent a vascular tangle of a plurality of human patients in a first group; 1320 achieving, by the n-BCA kit and the first microcatheter, approximately 53% reduction in preoperative embolization procedure cost for treating at least one blood vessels adjacent a vascular tangle versus a second group treated by an EVOH kit and a plug and push microcatheter; and 1330 achieving, by the n-BCA kit and the first microcatheter, approximately 79% reduction in preoperative embolization procedure cost for treating at least four blood vessels adjacent a vascular tangle versus a second group treated by an EVOH kit and a plug and push microcatheter. Method or use 1300 can end after step 1320 or after step 1330. In other embodiments, additional steps according to the examples described above can be performed.

FIG. 14 depicts a method or use 1400 and can include 1410 delivering, by a first microcatheter, a first embolic agent kit comprising the n-BCA kit within at least one blood vessel adjacent a vascular tangle of a first plurality of human patients in a first group; 1420 reducing a total cost of preoperative embolization procedure in the first group compared to a second group treated by delivering, by a balloon microcatheter, a second embolic agent kit comprising the EVOH kit within at least one blood vessel adjacent a vascular tangle; and 1430 reducing the total cost of preoperative embolization procedure by $2,487 per preoperative embolization procedure for the first group compared to the second group. Method or use 1400 can end after step 1430. In other embodiments, additional steps according to the examples described above can be performed.

FIG. 15 depicts a method or use 1500 and can include 1510 delivering, by a first microcatheter, a first embolic agent kit comprising the n-BCA kit within at least one blood vessel adjacent a vascular tangle of a first plurality of human patients in a first group; 1520 reducing a total cost of preoperative embolization procedure in the first group compared to a second group treated by delivering, by a detachable-tip microcatheter, a second embolic agent kit comprising the EVOH kit within at least one blood vessel adjacent a vascular tangle; and 1530 reducing the total cost of preoperative embolization procedure by $7,959 per preoperative embolization procedure for the first group compared to the second group. Method or use 1500 can end after step 1530. In other embodiments, additional steps according to the examples described above can be performed.

FIG. 16 depicts a method or use 1600 and can include 1610 delivering, by a first microcatheter, a first embolic agent kit comprising the n-BCA kit within at least one blood vessel adjacent a vascular tangle of a first plurality of human patients in a first group; 1620 reducing a total cost of preoperative embolization procedure in the first group compared to a second group treated by delivering, by a plug and push microcatheter, a second embolic agent kit comprising the EVOH kit within at least one blood vessel adjacent a vascular tangle; and 1630 reducing the total cost of preoperative embolization procedure by $6,770 per preoperative embolization procedure for the first group compared to the second group. Method or use 1600 can end after step 1630.

FIG. 17 depicts a method of use 1700 and can include 1710 reducing a total cost of preoperative embolization procedure for a plurality of human patients by delivering, by a first microcatheter, a first embolic agent kit comprising the n-BCA kit within at least one blood vessel adjacent a vascular tangle of each of the first plurality of human patients. Method or use 1700 can end after step 1710. The reduced costs of preoperative embolization procedure by delivering the n-BCA kit can range from approximately 30% to approximately 57%.

In other embodiments, additional steps according to the examples described above can be performed. The n-BCA liquid embolic agent and microcatheter techniques and related methods of use of this disclosure demonstrated cost savings compared to three common EVOH liquid embolization procedure techniques in patients with brain arteriovenous malformation (bAVM). The specific choice of liquid embolic agent and the type of microcatheter can be varied according to particular design specifications or constraints requiring a system or method constructed according to the principles of the disclosed technology. Such changes are intended to be embraced within the scope of the disclosed technology.

The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method or use of reducing a cost of embolization in a human patient at risk for intracranial hemorrhage, the method comprising:
   calculating a cost adjusted ratio for embolizing at least one blood vessel adjacent a vascular tangle in a first group of human patients with a first embolic agent comprising N-butyl cyanoacrylate (the "n-BCA") compared to embolizing at least one blood vessel adjacent a vascular tangle in a second group of human patients with a second embolic agent, wherein the cost adjusted ratio comprises conditions comprising at least one of:
      embolization procedure time,
      units of first or second embolic agent,
      concentration per unit of first or second embolic agent,
      type of catheter,
      number of catheters, and
      angiography suite time;
   identifying at least one condition in the cost adjusted ratio to achieve at least 18% reduced cost of the embolization of the first group compared to the second group, the cost adjusted ratio being determined by a Generalized estimating equations (GEE) model; and
   embolizing, by a first catheter, by delivering the n-BCA, adjusted by at least one condition, within at least one blood vessel adjacent a vascular tangle in a respective human patient.

2. The method or use according to claim 1, the first group of human patients comprising approximately 1,072 human patients from a plurality of different hospital sites.

3. The method or use according to claim 1, the first group of human patients comprising inclusion criteria defined as patients who underwent a preoperative embolization procedure for unruptured brain arteriovenous malformation between 2010-2020 and were identified from the Premier Healthcare Database.

4. The method or use according to claim 1, the first group of human patients comprising inclusion criteria defined as patients ≥18 years old at the time of index hospital admission.

5. The method or use according to claim 1, the first group of human patients comprising exclusion criteria defined as patients who had their index preoperative embolization procedure by delivering the n-BCA in combination with the second embolic agent comprising ethylene vinyl alcohol copolymer ("EVOH").

6. A method or use of reducing a cost of embolization in a human patient at risk for intracranial hemorrhage based on a comparison of costs for embolizing a first group of human patients compared to a second group of human patients treated with disparate embolic agents, the method comprising:
  comparing cost conditions of embolizing, the cost conditions comprising at least one of:
    embolization procedure time,
    units of a first embolic agent or a second embolic agent,
    concentration of the first embolic agent or the second embolic agent per unit,
    type of catheter,
    number of catheters, and
    angiography suite time; and
  reducing embolization procedure time while maintaining hospital length of stay by embolizing, by a first catheter, by delivering the first embolic agent comprising N-butyl cyanoacrylate (the "n-BCA") within at least one blood vessel adjacent a vascular tangle in a respective human patients.

7. The method or use according to claim 6,
  wherein the second group of human patients is treated by embolizing, by a second catheter, by delivering the second embolic agent comprising ethylene vinyl alcohol copolymer ("EVOH") within the least one blood vessel adjacent the vascular tangle, and
  wherein the embolization procedure time is at least 30% lower for the first group versus the second group.

8. The method or use according to claim 6,
  wherein the second group of human patients is treated by embolizing, by a third catheter, by delivering the second embolic agent comprising ethylene vinyl alcohol copolymer ("EVOH") within the least one blood vessel adjacent the vascular tangle, and
  wherein the embolization procedure time is at least 57% lower for the first group versus the second group.

9. The method or use according to claim 6,
  wherein the second group of human patients is treated by embolizing, by a fourth catheter, by delivering the second embolic agent comprising ethylene vinyl alcohol copolymer ("EVOH") within the least one blood vessel adjacent the vascular tangle, and
  wherein the embolization procedure time is at least 53% lower for the first group versus the second group.

10. The method or use according to claim 6, further comprising:
  achieving, by the n-BCA and the first catheter, approximately 67% lower preoperative embolization procedure time for treating at least four blood vessels adjacent a vascular tangle versus the second group treated by the second embolic agent comprising ethylene vinyl alcohol copolymer ("EVOH") and a second catheter.

11. The method or use according to claim 6, further comprising:
  achieving, by the n-BCA and the first catheter, approximately 81% lower preoperative embolization procedure time for treating at least four blood vessels adjacent a vascular tangle versus the second group treated by the second embolic agent comprising ethylene vinyl alcohol copolymer ("EVOH") and a third catheter.

12. The method or use according to claim 6, further comprising:
  achieving, by the n-BCA and the first catheter, approximately 79% lower preoperative embolization procedure time for treating at least four blood vessels adjacent a vascular tangle versus the second group treated by the second embolic agent comprising ethylene vinyl alcohol copolymer ("EVOH") and a fourth catheter.

13. The method or use according to claim 6,
  wherein the cost of the first embolic agent is at least 30% lower versus the cost of the second embolic agent.

14. The method or use according to claim 13, further comprising:
  delivering the second embolic agent comprising ethylene vinyl alcohol copolymer ("EVOH") by a balloon catheter to the second group, and
  achieving at least 30% reduced time for the first group versus the second group.

15. The method or use according to claim 13, further comprising:
  delivering the second embolic agent comprising ethylene vinyl alcohol copolymer ("EVOH") by a detachable-tip catheter to the second group, and
  achieving at least 57% reduced time for the first group versus the second group.

16. The method or use according to claim 13, further comprising:
  delivering the second embolic agent comprising ethylene vinyl alcohol copolymer ("EVOH") by a plug and push catheter to the second group, and
  achieving at least 53% reduced time for the first group versus the second group.

17. A method or use comprising:
  determining a ratio of cost conditions of embolizing a first group of human patients treated with a first embolic agent comprising N-butyl cyanoacrylate (the "n-BCA") compared to a second group of human patients treated with a second embolic agent comprising ethylene vinyl alcohol copolymer (the "EVOH"), the ratio of cost conditions comprising comparing n-BCA to EVOH for at least one of embolization procedure time, units of embolization agent, concentration of embolization agent per unit, type of catheter to deliver embolization agent, number of catheters to deliver embolization agent, and angiography suite time; and
  delivering, by a first catheter, the n-BCA, adjusted by at least one condition, within at least one blood vessel adjacent a vascular tangle of a respective human patient to achieve a reduced total cost of the embolization procedure in the respective human patient.

18. The method or use according to claim 17, further comprising:

achieving a reduced ratio of cost conditions of preoperative embolization procedure in the respective human patient by approximately $2,487 compared to the second group treated by delivering, by a balloon catheter, the EVOH within at least one blood vessel adjacent a vascular tangle, and wherein the total cost of the embolization procedure is adjusted for medical inflation and reported in 2020 US dollars ($).

19. The method or use according to claim 17, further comprising:

achieving a reduced ratio of cost conditions of preoperative embolization procedure in the respective human patient by approximately $7,959 compared to the second group treated by delivering, by a detachable-tip catheter, the EVOH within at least one blood vessel adjacent a vascular tangle, and wherein the total cost of the embolization procedure is adjusted for medical inflation and reported in 2020 US dollars ($).

20. The method or use according to claim 17, further comprising:

achieving a reduced ratio of cost conditions of preoperative embolization procedure in the respective human patient by approximately $6,770 compared to the second group treated by delivering, by a plug and push catheter, the EVOH within at least one blood vessel adjacent a vascular tangle, and wherein the total cost of the embolization procedure is adjusted for medical inflation and reported in 2020 US dollars ($).

21. A method or use of reducing a cost of embolization in a patient at risk for intracranial hemorrhage, the method comprising:

calculating a cost adjusted ratio for a condition comprising at least one of embolization procedure time, units of a first or second embolization agent, concentration of the first or second embolization agent per unit, type of catheter, number of catheters, and angiography suite time between a first group of human patients treated with the first embolic agent compared to a second group of human patients treated with a second embolic agent;

delivering, by a first catheter, the first embolic agent within at least one blood vessel adjacent a vascular tangle of a respective human patient; and reducing at least one condition to achieve a difference in cost of preoperative embolization procedure for the respective human patient from approximately 30% to approximately 57%, by the first embolic agent, wherein the first embolic agent comprises N-butyl cyanoacrylate (the "n-BCA") and the second embolic agent comprises ethylene vinyl alcohol copolymer (the ("EVOH").

22. The method or use according to claim 21, comprising: achieving at least 30% reduced cost for the respective human patient treated with the n-BCA versus delivering, by a balloon catheter, the EVOH.

23. The method or use according to claim 21, comprising: achieving at least 57% reduced cost for the respective human patient treated with the n-BCA versus delivering, by a detachable-tip catheter, the EVOH.

24. The method or use according to claim 21, comprising: achieving at least 53% reduced cost for the respective human patient treated with the n-BCA versus delivering, by a plug and push catheter, the EVOH.

* * * * *